United States Patent
Owens

Patent Number: 5,287,860
Date of Patent: Feb. 22, 1994

[54] BIRTHING DRAPE

[76] Inventor: Rebecca L. Owens, 1260 No Pone Rd., NW., Georgetown, Tenn. 37336

[21] Appl. No.: 955,934

[22] Filed: Oct. 2, 1992

[51] Int. Cl.$^5$ .............................................. A61B 19/08
[52] U.S. Cl. .................... 128/851; 128/849; 128/856
[58] Field of Search ................ 128/846, 849, 851-853, 128/856; 604/327, 329, 356, 357

[56] References Cited

U.S. PATENT DOCUMENTS

| | | | |
|---|---|---|---|
| 1,230,756 | 6/1917 | Mohler | 604/357 |
| 3,386,444 | 6/1968 | Brenner et al. | 604/357 |
| 3,452,750 | 7/1969 | Blanford | 128/853 |
| 4,007,741 | 2/1977 | Waldrop et al. | 604/357 |
| 4,221,371 | 9/1980 | Kuphal | 604/356 X |
| 4,378,794 | 4/1983 | Collins | 128/853 |
| 4,598,458 | 7/1986 | McAllester | 128/853 |
| 4,869,271 | 9/1989 | Idris | 128/853 |
| 4,880,418 | 11/1989 | Tramont | 604/356 |
| 4,903,710 | 2/1990 | Jessamine et al. | 128/849 |
| 4,926,882 | 5/1990 | Lawrence | 128/850 |
| 5,002,069 | 3/1991 | Thompson et al. | 128/849 |
| 5,027,832 | 7/1991 | Williams, Jr. | 128/849 |
| 5,107,859 | 4/1992 | Alcorn et al. | 128/849 X |

*Primary Examiner*—Robert A. Hafer
*Assistant Examiner*—Brian E. Hanlon
*Attorney, Agent, or Firm*—Alan Ruderman

[57] ABSTRACT

A birthing drape for catching body fluids expelled during birth and for precluding the fluids from splashing onto assisting personnel has a web of plastic material having first and second spaced apart ends and a pair of laterally spaced apart edges extending between the first and second ends. A support portion upon which the buttocks of a birthing woman may be positioned is defined at one end and a catch portion extends from the support portion to the second end. A splash guard in the form of a bulbous formation is formed at the second end and an opening is formed in the catch portion between the support portion and the splash guard. The opening has a mouth for receiving and storing body fluids. Elastic strips extend within pockets along the respective lateral edge, each strip having an end secured to the support portion and to the catch portion adjacent the splash guard but being free to move within the remainder of the respective pocket. The length of each strip when expanded is approximately equal to the relaxed length of the edge between the fixed ends so that in the contracted or relaxed condition of the strips the lateral edges of the catch portion are puckered and the splash guard is drawn toward the support portion. Bands are connected to the catch portion and adapted to encircle the ankles of the woman so as to open the mouth and raise the splash guard to deflect fluids into the catch portion.

16 Claims, 2 Drawing Sheets

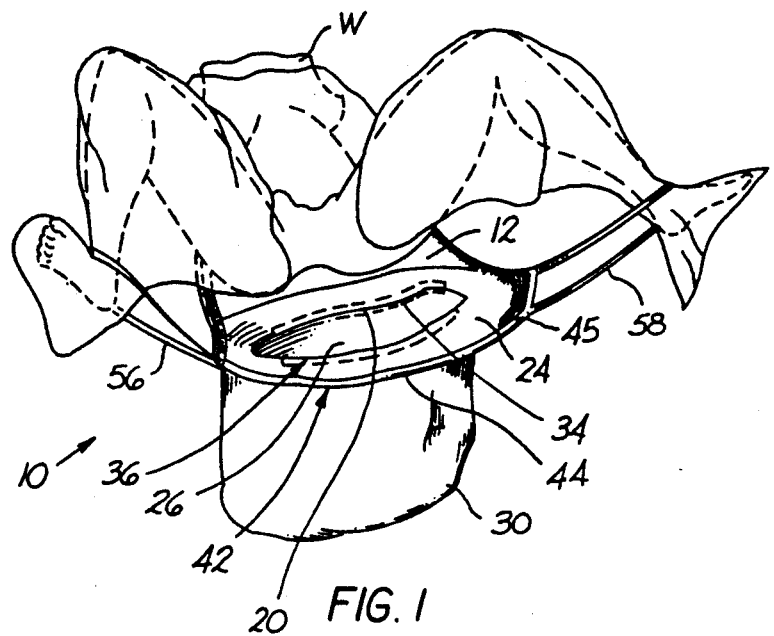
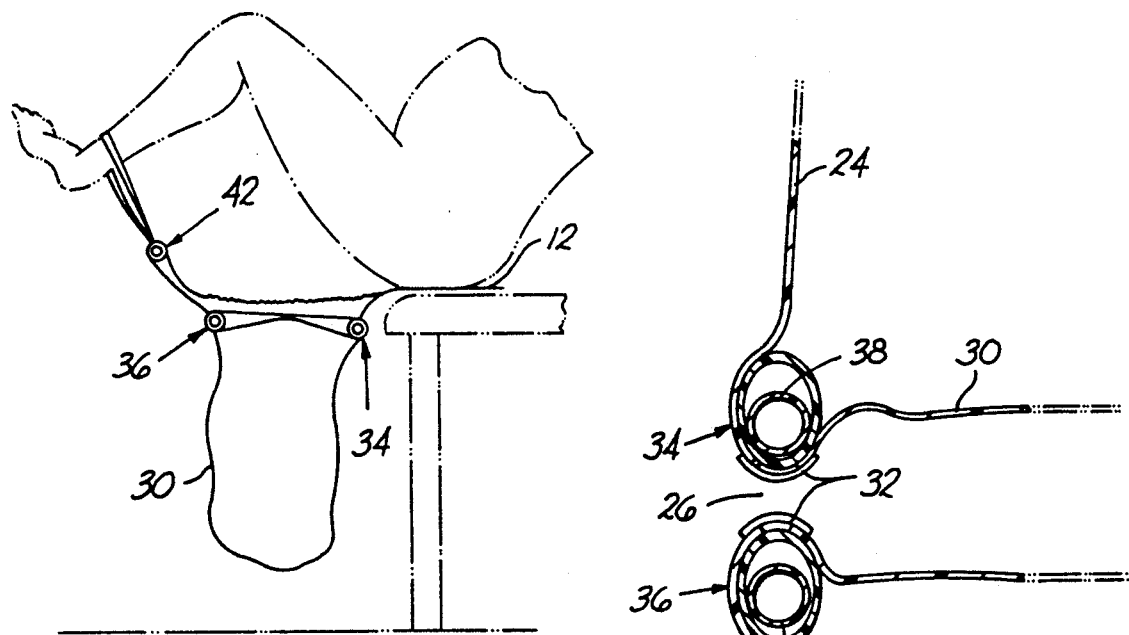

BIRTHING DRAPE

BACKGROUND OF THE INVENTION

This invention relates to a birthing drape having a portion positionable under the buttocks of a birthing woman and including a pouch for catching blood and other body fluids, the drape having a splash guard for directing splashing fluid into the pouch.

During the birthing process when a baby is being delivered body fluids including blood are expelled with the baby. In the prior art the delivering woman may be positioned with her legs in stirrups and have one end of a rectangular plastic drape under her buttocks, another end of the drape being disposed downwardly in a catch basket so that the body fluids flow downwardly into the bucket. This inefficient approach to catching the body fluids results in fluids escaping onto the floor especially splashing fluids. As a result of the recent HIV and AIDS epidemic it is now known that such escaping fluids create major health risks for hospital staff members. An attempt to solve this escaping fluid problem has resulted in a birthing drape having a built-in pouch for catching the body fluids. The drape has a trapezoidal shape on which the buttocks rests and the pouch merely hangs downwardly from the central portion. One difficulty with this construction is that the pouch tends to close. Another difficulty is that splashing fluids are not contained and they readily splash on staff members.

SUMMARY OF THE INVENTION

Consequently, it is a primary object of the present invention to provide a birthing drape having a portion on which the buttocks of a birthing woman rests and having a pouch adjacent thereto, the pouch having a mouth formed by enlarged lips, and resilient members extendible to open the pouch and separate the lips while contouring the mouth to a disposition for aiding in directing body fluids from the woman into the pouch.

It is another object of the present invention to provide a birthing drape having a support portion on which the buttocks of a birthing woman may rest, the drape having a pouch adjacent the support portion including a mouth having one lip adjacent the support portion and a second lip remote from the support portion, and including a splash guard spaced from the second lip remote from the support portion, the disposition of the splash guard being controlled by resilient members extendible to raise the splash guard above the mouth.

It is a further object of the present invention to provide a birthing drape having a support portion on which a birthing woman may be positioned, the drape having a pouch adjacent the support portion including a mouth formed by enlarged lips, one lip being adjacent the support portion and another lip remote from the support portion, a splash guard spaced from the second lip remote from the support portion, and resilient members extendible to open the pouch and separate the lip while contouring the mouth and raising the splash guard above the mouth to direct body fluids from the woman to the mouth into the pouch.

Accordingly, the present invention provides a birthing drape for catching body fluids expelled during birth from a birthing woman and for precluding the fluids from splashing onto staff personnel assisting in the birth. The drape comprises a web having a first portion on which the buttocks of the birthing woman may be disposed, a second portion spaced from the first portion including a splash guard on the second portion remote from the first portion. An opening is formed in the web intermediate the first portion and the splash guard, the opening forming the mouth of a pouch into which body fluids and the like may be received. The mouth includes a first lip adjacent to the first portion and a second lip adjacent the second portion. Elastomeric members extend along spaced edges of the first and second portions and have respective ends fixed to the first and second portions, the elastomeric members acting to normally pull the edges of the second portion toward the first portion and pleat or pucker the edges of the second portion so as to crater the second portion into the form of a basin. Strap means are connected to the second portion and are receivable about the legs of the woman so as to extend the elastomeric material and thereby separate the lips and open the mouth of the pouch. Extension of the elastomeric material also reconfigures the second portion and lifts the splash guard to direct splashing fluids onto the second portion and into the pouch.

The lips of the mouth preferably have a bulbous configuration to better form and open the mouth and to preclude inadvertent closing thereof, while the splash guard is also of a bulbous configuration disposed at the end of the second portion remote from the first portion.

BRIEF DESCRIPTION OF THE DRAWINGS

The particular features and advantages of the invention as well as other objects will become apparent from the following description taken in connection with the accompanying drawings in which:

FIG. 1 is a perspective view of a birthing drape formed in accordance with the principles of the present invention illustrated in the operative position;

FIG. 3 is a cross sectional view taken substantially along line 3—3 of FIG. 2 but in the operative position;

FIG. 4 is a cross sectional view taken substantially along line 4—4 of FIG. 2;

DESCRIPTION OF THE PREFERRED EMBODIMENT

Figure 2:
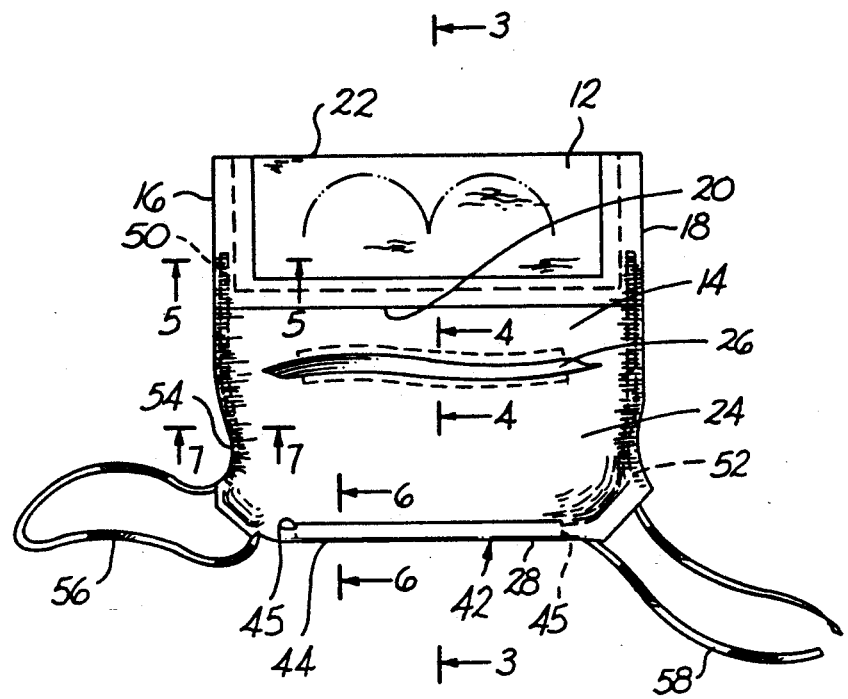
FIG. 2 is a top plan view of the drape in an inoperative position.
Figure 5:
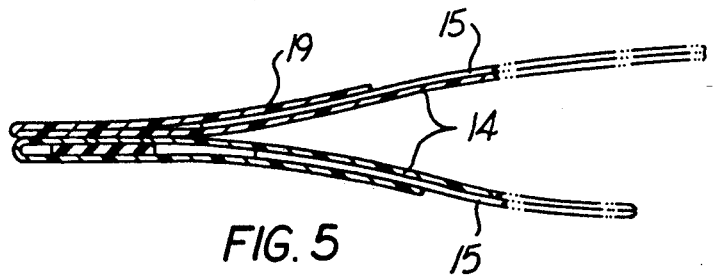
FIG. 5 is a cross sectional view taken substantially along line 5-5 of FIG. 2.
Figure 6:
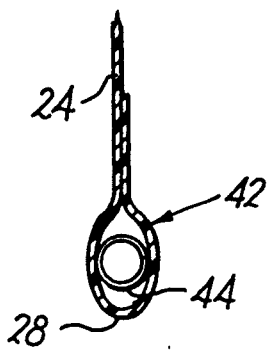
FIG. 6 is a cross sectional view taken substantially along line 6-6 of FIG. 2.
Figure 7:
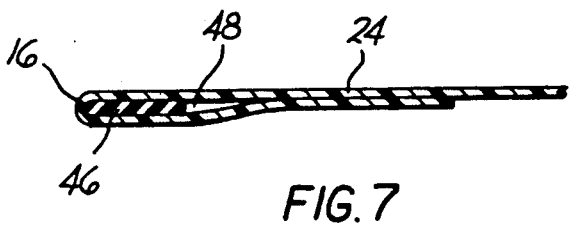
FIG. 7 is a cross sectional view taken substantially along line 7-7 of FIG. 2.

Referring now to the drawings, FIG. 1 illustrates a birthing drape 10 constructed in accordance with the present invention, the drape being illustrated in the operative position with the buttocks of a woman W positioned on a support portion 12 disposed on a birthing table. The drape, as best illustrated in FIG. 2, comprises a substantially rectangular web of material 14, preferably synthetic plastic such as polyethylene, having the support portion formed at one end of the web. The support portion preferably includes a sheet of soft absorbent fibrous material 15, illustrated in FIG. 5, extending between and spaced slightly from the lateral edges 16, 18 of the web and extending from one longitudinal edge 20 to a longitudinal location spaced from the edge 20, the material 14 being attached at its borders to the web by adhesive tape 19 or the like. The support portion of the web together with the absorbent material 14 has a fold which forms one end 22 of the drape so that the longitudinal edge 20 of the web is superposed over the spaced edge of the absorbent material and the lateral edges are bonded or taped together. The edge 20, however, is not connected to the web portion over which it is disposed so that a useful pocket may be formed therebetween. The absorbent material is disposed on both the top and bottom of the support portion and thus may engage the birthing table and the buttocks of the woman.

Formed by the web adjacent to the support portion 12 is a catch portion 24 of the drape. A laterally elongated opening 26 is formed in the catch portion longitudinally intermediate the support portion 12 and the second end 28 of the drape. The opening may merely be a slit in the catch portion with the lateral ends spaced from the lateral edges 16, 18 of the web. A pouch 30 in the form of a plastic bag such as a polyethylene bag is disposed with the periphery of its mouth about the periphery of the opening 26 and secured thereto with adhesive tape 32 or the like which extends entirely about the periphery of the opening and the pouch. A pair of spaced apart lips 34, 36 are formed at the longitudinally leading and trailing edges respectively of the opening 26 to define the mouth of the opening.

Each lip 34, 36 is formed into an enlarged or bulbous configuration preferably by a roll 38, 40 of material in the central portion of each lip, which may be rolled webs of plastic material disposed in the laterally central portion of the leading and trailing edges and held in place by wrapping or encircling the adjacent portion of the respective leading edge of the web about the roll prior to applying the tape 32. Of course, other convenient means for entrapping the respective rolls between the material forming the leading edges of the opening and the adjacent periphery of the pouch may be utilized in accordance with the present invention so that the rolls are internally of the mouth of the opening. The rigidity of the enlarged lips 34, 36 act to hold the mouth of the opening in an open position when the pouch is disposed downwardly in the operative disposition and prevents the mouth from inadvertently closing. Thus, rather than rolls, other rigid members about the leading and trailing edges are contemplated by the invention. For example, wire or plastic frames may serve the same functional effect.

Spaced from the opening 26 at the second edge 28 of the drape is another bulbous section defining a splash guard 42 which is also preferably formed from a roll 44 of plastic material about which the end of the web is wrapped and held in place by adhesive tape or the like. The roll 44 forming the splash guard is in the central portion of the edge 28 and does not extend to the lateral edges but terminates at locations 45 spaced therefrom. The splash guard 42 is thus at the end of the catch portion 24 spaced from the opening 26 remote from the support portion 12 to form the catch portion into a basin shape and elevate the splash guard relative to the central portion of the basin.

Resilient members in the form of elastomeric strips such as stretchable elastic fabric 46 are disposed along each lateral edge of the catch portion, each strip having one end fixed to the catch portion at or adjacent the second end 28 of the drape and another end fixed to the support portion. Each elastomeric strip 46 is disposed along the respective edge 16, 18 and entrapped within a respective pocket 48 formed by folding the edges of the web on itself so that the elastomeric strip is contained within the pocket. One end 50 of the elastic strip is secured within a pocket to the support portion 12 and the other end 52 is secured within a pocket adjacent the end 28 of the drape, while the remainder of each strip is free to move within the respective pocket in the catch portion. The length of each strip 46 in its expanded condition is substantially equal to the length of the edges 16, 18 of the drape at the ends 50, 52. Thus, in the relaxed condition of the strips the length of each strip 46 is less than the spacing between the ends 50 and 52 so that in the relaxed condition the end 52 is drawn toward the end 50 and the edges 16 and 18 of the catch portion 24 are pulled toward the support portion and are pleated, as illustrated at 54 in FIG. 2, thereby forming the catch portion into a substantially concave or basin shape. This also tends to bend the ends of the splash guard and elevate the splash guard relative to the formed basin since it is at the end of the drape.

Secured to the lateral edges 16, 18 adjacent the end 28 of the drape is a respective band 56, 58, each of which preferably comprises a pair of elastic strips having ends adjustably connected together by hook and loop fastener members such as that sold under the VELCRO brand name. The bands are adapted to encircle the ankles or legs of the woman while in the birthing position wherein the legs are in stirrups of the birthing table. The length of the bands 56, 58 are such that when in the birthing position the bands are pulled thereby expanding the strips 46 as illustrated in FIGS. 1 and 3. This tends to stretch the pleats at the edges 16, 18 of the catch portion and fully opens the mouth of the opening 26 while simultaneously raising the splash guard 42 and cupping the catch portion along the edges and between the locations 45 and the edges, thereby to further contour and crater the catch portion into a basin shape. Thus, fluids expelled from the baby flow into the mouth of the opening 26 and into the pouch 30 and fluids splashing forwardly are funneled by the splash guard and the basin shape of the catch portion into the opening 26 and into the pouch 30.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A birthing drape for catching and storing body fluids expelled during the birthing process comprising, a web of material having first and second ends and a pair of laterally spaced apart edges extending from said first end to said second end, a support portion at said first end upon which the buttocks of a birthing woman may rest, a catch portion extending from the support portion to said second end, a splash guard on the catch portion at said second end, an opening having a mouth formed in the catch portion intermediate said support portion and said splash guard, a pouch having an open entry end including a periphery fixed to and disposed about said mouth and a closed end for receiving and retaining said fluids, expandable resilient means at each lateral edge for pulling said edges adjacent said splash guard toward said support portion and for cratering said catch portion into a substantially basin shaped configuration, and band means secured to said catch portion adjacent said second end and each of said edges for encircling the lower limbs of said woman for drawing said resilient means from a contracted to an expanded condition to lift the lateral edges and said splash guard relative to the remainder of said catch portion, whereby expelled fluids are directed and funneled toward and into said pouch.

2. A birthing drape as recited in claim 1, wherein said resilient means comprises an elastomeric member having a first terminus secured to said support portion at a first location and a second terminus secured to said catch portion at a second location adjacent said second end, each member being expandable location adjacent said from a contracted condition to an expanded condition, the length of each member in the expanded condition being substantially equal to the relaxed length of the lateral edge between said first and second locations such that said second location is pulled toward said first location to reduce said length and pucker the edge when the respective member is in the contracted condition, and means for entrapping each elastomeric member along a lateral edge of said catch portion intermediate the first and second locations.

3. A birthing drape as recited in claim 2, wherein said splash guard comprises a bulbous formation, said formation being rigid relative to the web.

4. A birthing drape as recited in claim 3, wherein said mouth includes means defining a pair of spaced apart rigid lips.

5. A birthing drape as recited in claim 4, wherein each of said lips comprises a bulbous formation.

6. A birthing drape as recited in claim 2, wherein said elastomeric members are relaxed in the contracted condition and are stretched in the expanded condition.

7. A birthing drape as recited in claim 6, wherein said splash guard comprises a bulbous formation, said formation being rigid relative to the web.

8. A birthing drape as recited in claim 6, wherein said mouth includes means defining a pair of spaced apart rigid lips.

9. A birthing drape as recited in claim 8, wherein each of said lips comprises a bulbous formation.

10. A birthing drape as recited in claim 2, wherein said means for entrapping each elastomeric member comprises a pocket formed along the respective lateral edge.

11. A birthing drape as recited in claim 10, wherein said elastomeric members are relaxed in the contracted condition and are stretched in the expanded condition.

12. A birthing drape as recited in claim 1, wherein said splash guard comprises a bulbous formation, said formation being rigid relative to the web.

13. A birthing drape as recited in claim 12, wherein said bulbous formation comprises a roll of web material.

14. A birthing drape as recited in claim 1, wherein said mouth includes means defining a pair of spaced apart rigid lips.

15. A birthing drape as recited in claim 14, wherein each of said lips comprises a bulbous formation.

16. A birthing drape as recited in claim 15, wherein each bulbous formation comprises a roll of web material.

* * * * *